United States Patent
Bastiaensen et al.

(10) Patent No.: US 7,459,669 B2
(45) Date of Patent: Dec. 2, 2008

(54) SENSOR AND LITHOGRAPHIC APPARATUS

(75) Inventors: Rob Adrianus Antonius Maria Bastiaensen, Zundert (NL); Marcel Maurice Hemerik, Helmond (NL); Marcus Adrianus Van De Kerkhof, Helmond (NL); Jeroen Johannes Sophia Maria Mertens, Duizel (NL); Jacob Sonneveld, Best (NL)

(73) Assignee: ASML Netherlands B.V., Veldhoven (NL)

( * ) Notice: Subject to any disclaimer, the term of this patent is extended or adjusted under 35 U.S.C. 154(b) by 0 days.

(21) Appl. No.: 11/321,466

(22) Filed: Dec. 30, 2005

(65) Prior Publication Data

US 2007/0152178 A1    Jul. 5, 2007

(51) Int. Cl.
*G03B 27/42*    (2006.01)
*G03F 7/20*    (2006.01)
(52) U.S. Cl. .................. 250/216; 250/487.1; 355/53
(58) Field of Classification Search ............... 250/216, 250/483.1, 484.5, 487.1; 355/53
See application file for complete search history.

(56) References Cited

U.S. PATENT DOCUMENTS

| 2002/0001088 | A1 | 1/2002 | Wegmann et al. |
| 2005/0237504 | A1* | 10/2005 | Nagasaka et al. ............ 355/53 |
| 2005/0243328 | A1* | 11/2005 | Wegmann et al. .......... 356/520 |
| 2006/0181690 | A1* | 8/2006 | Nishinaga et al. ............ 355/53 |
| 2007/0070323 | A1* | 3/2007 | Nagasaka .................... 355/71 |

FOREIGN PATENT DOCUMENTS

| EP | 1 510 870 A1 | 3/2005 |
| JP | 62-121417 | 6/1987 |
| JP | 8-298747 | 11/1996 |

\* cited by examiner

*Primary Examiner*—John R Lee
(74) *Attorney, Agent, or Firm*—Pillsbury Winthrop Shaw Pittman LLP

(57) ABSTRACT

A sensor for use in a lithographic apparatus, the sensor having a liquid to prevent optical losses, especially when receiving radiation with a high NA. The liquid is fixed between two surfaces by capillary forces in an area through which radiation passes.

33 Claims, 8 Drawing Sheets

SENSOR AND LITHOGRAPHIC APPARATUS

FIELD

The present invention relates to a sensor usable in a lithographic apparatus and a lithographic apparatus.

BACKGROUND

A lithographic apparatus is a machine that applies a desired pattern onto a substrate, usually onto a target portion of the substrate. A lithographic apparatus can for example be used when manufacturing integrated circuits (ICs). In general, a patterning device, which is alternatively referred to as a mask or a reticle, may be used to generate a circuit pattern to be formed on an individual layer of the IC. This pattern can be transferred onto a target portion (e.g. comprising part of, one, or several dies) of a substrate (e.g. a silicon wafer). The transfer of the pattern is typically carried out by imaging it onto a layer of radiation-sensitive material (resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the "scanning"-direction) while synchronously scanning the substrate parallel or anti-parallel to this direction.

The radiation used to expose the target portion with a pattern is projected by a projection system. In order to obtain small resolutions, high numerical apertures (NA) are applied in such projection systems. However, in such a lithographic apparatus, frequently sensors are used that measure different parameters under such high NA conditions. A first example is a sensor that measures the aberrations of the projection system, such as described in U.S. published application 2002-0001088 A1. A second example is a transmission image sensor that measures the position of an image of the pattern formed relative to the substrate, such as described in EP1 510 870 A 1.

Such sensors, described in U.S. published application 2002-0001088 A1 and EP 1 510 870 A1, have to be able to effectively measure high NA radiation impinging on the sensor. When the sensors are not designed for use with high NA radiation, radiation will be lost and less accurate measurements may be performed. Loss of radiation may occur because of scattering at a rough surface within the sensor. It may also occur because of reflection at an optically smooth interface with a refractive index mismatch, i.e. an interface between two materials with smooth surfaces, but having a large difference in refractive index. A third cause of loss of radiation is total internal reflection at the interface between a material with a high refractive index and a low refractive index. This may cause radiation to leave the layer with the high refractive index on a side perpendicular to the interface after reflection of the radiation towards the side. With the radiation intended to cross the interface, radiation leaving the layer with the high refractive index on the side is lost. A fourth cause of loss of radiation is absorption in air gaps within the sensor. The air gaps cannot easily be purged and therefore may contain air and water, which absorb radiation of 157 nm wavelength. This is a typical wavelength for irradiating a target portion with a pattern.

EP 1 510 870 A1 discloses a sensor for use in a lithographic apparatus arranged to avoid loss of radiation within the sensor. It proposes to use filler layers in the sensor to avoid these problems. It, for instance, suggests using liquids such as Fomblin to form the filler layers. However, EP 1 510 870 A1 does not disclose how the liquids can be contained in the sensor. It is necessary to make sure that the liquid is kept at its intended position because the sensor is typically mounted on a substrate support table that moves at high speed. For instance, the substrate support table is moved at high speed while stepping to bring a second target portion below the projection system, after the first target portion has been irradiated. Thus, if the liquid is not properly contained, it flows away from its intended position during such a movement.

At first, seals were considered for sealing the liquid inside the sensor thereby solving the above drawback. During production of a sensor, there are always tolerances. The height of the filler layer is subject to tolerances as well. Therefore, when designing parts to seal the liquid inside the sensor, these height tolerances must be accounted for. Therefore flexible seals were considered.

A problem with the use of flexible seals, such as those made from rubber, within a sensor as disclosed above in EP 1 510 870 A1, is that flexible seals comprise molecules that gas out. In a lithographic apparatus, the environmental conditions are controlled with high accuracy to obtain very small patterns consistently at high yield. Variations in the material between the projection lens and the substrate cause variations in the index of refraction experienced by the radiation beam. This will cause variations in the image of the circuit pattern formed on the layer of radiation-sensitive material. Molecules that have gassed out of the flexible seals cause such variations in the material. Moreover, a lithographic apparatus normally comprises many very sensitive parts, such as interferometers, optical level sensors and optical alignment sensors. On all these sensitive parts, the gassed out molecules could form sediments, influencing the performance of the parts. A lithographic apparatus is regularly placed in a foundry that also houses other very sensitive apparatus, which performance may be negatively influenced by gasses entering those other apparatus. Thus, the lithographic apparatus should fulfill extremely tight specifications to reduce influencing the environment, such as by releasing materials. Having these kinds of molecules gassing out of a flexible seal into a lithographic apparatus is therefore considered as highly undesirable contamination of the machine. Other drawbacks exist with known systems.

SUMMARY

The invention provides a sensor that is useable in a lithographic apparatus, including a first member with a first surface and a second member with a second surface and comprising a liquid between the first surface and the second surface, wherein the first surface and the second surface are arranged to exert capillary forces on the liquid.

By nature, capillary forces can not gas out. Therefore, by containing the liquid between the first surface and second surface using capillary forces exerted by the first and second surface, there is no flexible seal and no gassing out is involved.

In a further, second embodiment of the invention, the sensor is arranged to exert the capillary forces via a predetermined first area of the first surface. If the complete space between the first surface and the second surface is not filled with liquid, liquid corresponding to the first area will be contained, thereby creating a preferential position for the liquid.

When the first surface has a protrusion in the first area protruding towards the second surface, the protrusion decreases the distance between the first area and the second surface, thereby increasing the capillary forces exerted by the first area and second surface.

In a third embodiment of the invention, the sensor is arranged to transmit optical radiation that is measured via an optical volume at a predetermined position between the first surface and the second surface, which optical volume is completely filled with the liquid. In this embodiment, there is an overflow volume which is connected to the optical volume by a first connection area through which the liquid can flow. The first surface and the second surface are arranged to pull the liquid from the overflow volume to the optical volume by the capillary forces.

A sensor according to this embodiment can be filled with liquid relatively easily. This is advantageous for a sensor being arranged to transmit optical radiation to be measured via the liquid filling an optical volume at a predetermined position (between the first and second surface) because the amount of liquid needed to fill the optical volume may vary due to tolerances. The amount of liquid supplied may vary due to tolerances as well. When the liquid is supplied during production, the liquid may not completely fill the optical volume or may overfill the optical volume and flow to unwanted positions. In the embodiment, when more liquid is supplied to the optical volume than needed to fill the optical volume, the liquid flows through the first connection area into the overflow volume. Therefore, an excess of liquid can be supplied without the liquid flowing to unwanted positions.

The capillary forces pull the liquid from the overflow volume to the optical volume until the optical volume is completely filled with liquid. Therefore, an excess of liquid can be supplied so that at least the optical volume is filled without detrimental effect of excess liquid.

In a fourth embodiment, the first area of the first surface comprises an optical area optimized to transmit optical radiation to be measured by the sensor and the first area comprises a barrier area surrounding the optical area, wherein higher capillary forces are exerted via the barrier area than through the optical area.

This is advantageous because the liquid is prevented from flowing out of the optical area by capillary forces exerted via the barrier area. The barrier area does not have to fulfill optical requirements and can be optimized for exerting capillary forces. The optical volume does not have to fulfill requirements to enable capillary forces to prevent the liquid from leaving the optical volume and can thus be optimized for optical performance.

In a fifth embodiment of the invention, a first treatment area in the first area of the first surface may receive a first treatment that increases the capillary forces exerted by the first surface on the liquid.

The higher the capillary forces exerted on the liquid in the first treatment area, the more force that needs to be applied to the liquid to have the liquid flow away from the first treatment area. Therefore, applying a treatment to the first treatment area in the first area, which increases the capillary forces exerted by the first treatment area in the first area, increases the force needed to be applied for the liquid to flow away form the first area.

In a sixth embodiment of the invention, a second treatment area of the first surface outside the first area may receive a second treatment, thereby decreasing the capillary forces exerted by the first surface on the liquid.

The lower the capillary forces exerted by the first surface outside the first area, the more force that needs to be applied to the liquid to have the liquid flow away from the first area. Therefore, a second treatment on the second treatment area to decrease the capillary forces that the second treatment area of the first surface may exert on liquid outside the first area, increases the force needed to have the liquid flow away from the first area to the second treatment area.

In a seventh embodiment of the invention, an intermediate part is provided between the first surface and the second surface, the intermediate part includes a third surface that faces the first surface and is arranged to exert capillary forces on the liquid between the first surface and the third surface.

In this embodiment, the liquid is contained by capillary forces that are exerted between the first member and the intermediate part. Therefore, the second surface does not have to be arranged close to the first surface, allowing for production tolerances in the distance between the first surface and the second surface.

In an eight embodiment of the invention, there are a plurality of intermediate bodies arranged between the first surface and the second surface to surround the liquid. The plurality of intermediate bodies are arranged to exert capillary forces on the liquid between neighboring intermediate bodies.

Since the neighboring intermediate bodies exert capillary forces on the liquid between them, a force higher than those capillary forces is needed to have the liquid pass the intermediate bodies. Since the intermediate bodies are between the first and second surface and surround the liquid, and liquid can not pass neighboring intermediate bodies, the liquid is contained by the intermediate bodies.

In a ninth embodiment of the invention, a sensor is provided that is usable in a lithographic apparatus, the sensor includes a first member and a second member for fixing a liquid between the first surface and the second surface by capillary forces.

By nature, capillary forces can not gas out. Therefore, by containing the liquid between the first member and second member by capillary forces, there is no gassing out.

In a tenth embodiment of the invention, the first member has a first surface and the second member has a second surface. The first member has a protrusion of the first surface protruding towards the second surface and is arranged to increase fixation of the liquid by capillary forces.

Where the protrusion protrudes towards the second surface, the distance between the protrusion and the second surface is relatively small. Since the distance is relatively small, less liquid has to be fixed in place. Less capillary forces are needed to fix less liquid.

In an eleventh embodiment of the invention, the first surface is at least partially treated to increase the capillary forces between the first surface and the second surface. This is advantageous because higher capillary forces improve containment of the liquid between the first and second surfaces.

In a twelfth embodiment of the invention, the first surface is at least partially treated to decrease the capillary forces existing between the first surface and the second surface. This is advantageous to avoid liquid remaining between the first surface and the second surface where the first surface is treated. The liquid will flow to untreated areas where the capillary forces are higher.

In a thirteenth embodiment of the invention, the sensor includes an intermediate part having a third surface between the first surface and the second surface, the third surface facing the first surface, and being arranged to exert capillary forces on the liquid between the first surface and the third surface.

In this embodiment, the liquid is contained by capillary forces that are exerted between the first member and the intermediate part. Therefore, the second surface does not need to be arranged close to the first surface, allowing for production tolerances in the distance between the first surface and the second surface.

In a fourteenth embodiment of the invention, a plurality of intermediate bodies are arranged between the first surface and the second surface to surround the liquid. The plurality of intermediate bodies are arranged to exert capillary forces on the liquid between neighboring intermediate bodies.

Since the neighboring intermediate bodies exert capillary forces on the liquid between them, a force higher than those capillary forces is needed to have the liquid pass the intermediate bodies. Since the intermediate bodies are between the first and second surface and surround the liquid, and liquid can not pass neighboring intermediate bodies, the liquid is contained by the intermediate bodies.

A lithographic apparatus that includes a sensor according to the invention does not need to be stopped during production to put liquid at the first area. Thus, production throughput of the lithographic apparatus may be increased.

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION

Figure 1:
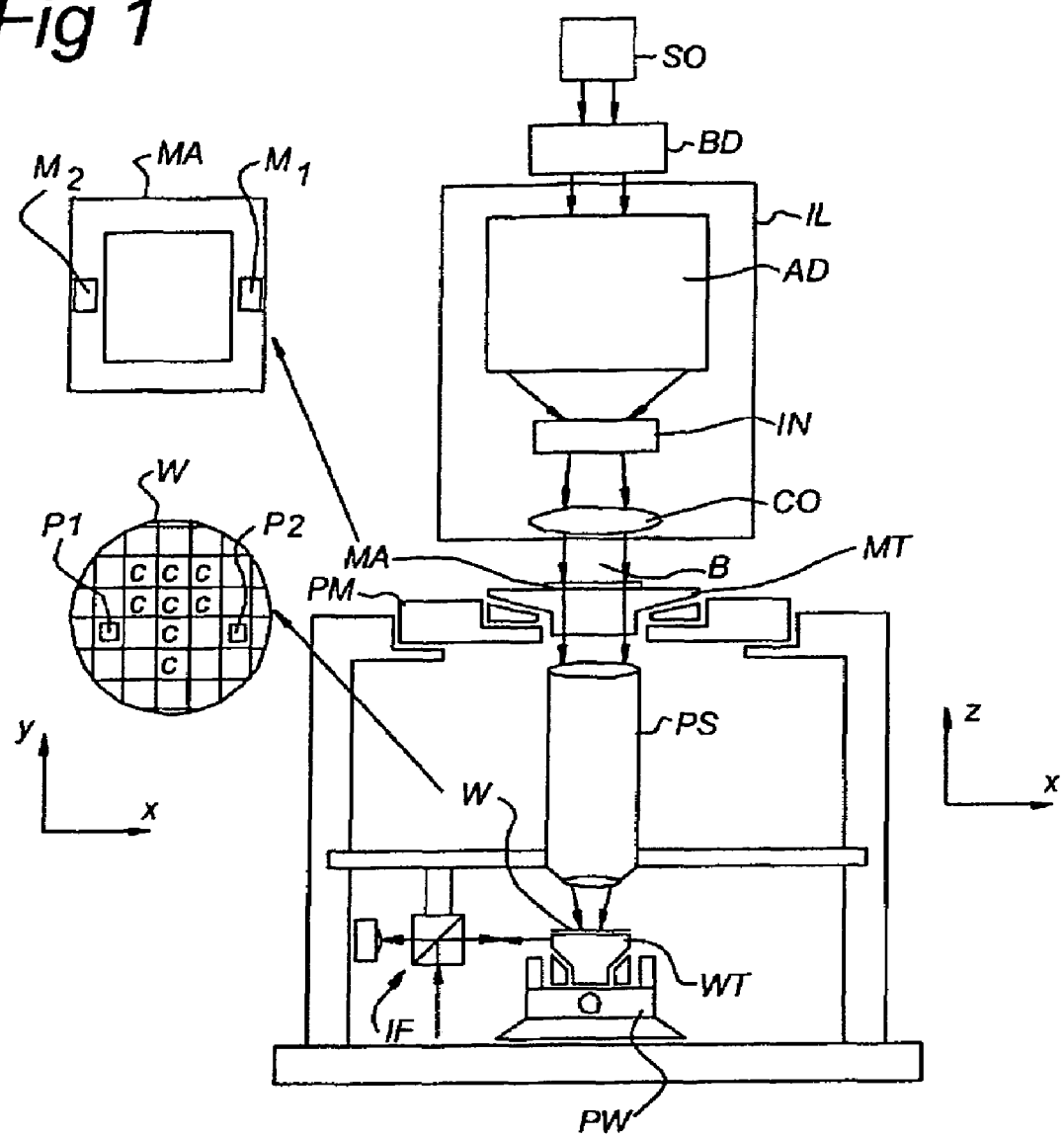
FIG. 1 depicts a lithographic apparatus according to an embodiment of the invention.

FIG. 1 schematically depicts a lithographic apparatus according to one embodiment of the invention. The apparatus includes:

an illumination system (illuminator) IL configured to condition a radiation beam B (e.g. UV radiation or DUV radiation).

a support structure (e.g. a mask table) MT constructed to support a patterning device (e.g. a mask) MA and connected to a first positioner PM configured to accurately position the patterning device in accordance with certain parameters;

a substrate table (e.g. a wafer table) WT constructed to hold a substrate (e.g. a resist-coated wafer) W and connected to a second positioner PW configured to accurately position the substrate in accordance with certain parameters; and a projection system (e.g. a refractive projection lens system) PS configured to project a pattern imparted to the radiation beam B by patterning device MA onto a target portion C (e.g. comprising one or more dies) of the substrate W.

The illumination system may include various types of optical components, such as refractive, reflective, magnetic, electromagnetic, electrostatic or other types of optical components, or any combination thereof, for directing, shaping, or controlling radiation.

The support structure supports, i.e. bears the weight of, the patterning device. It holds the patterning device in a manner that depends on the orientation of the patterning device, the design of the lithographic apparatus, and other conditions, such as for example whether or not the patterning device is held in a vacuum environment. The support structure can use mechanical, vacuum, electrostatic or other clamping techniques to hold the patterning device. The support structure may be a frame or a table, for example, which may be fixed or movable as required. The support structure may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam which is reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the apparatus is of a transmissive type (e.g. employing a transmissive mask). Alternatively, the apparatus may be of a reflective type (e.g. employing a programmable mirror array of a type as referred to above, or employing a reflective mask).

The lithographic apparatus may be of a type having two (dual stage) or more substrate tables (and/or two or more mask tables). In such "multiple stage" machines the additional tables may be used in parallel, or preparatory steps may be carried out on one or more tables while one or more other tables are being used for exposure.

The lithographic apparatus may also be of a type wherein at least a portion of the substrate may be covered by a liquid having a relatively high refractive index, e.g. water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems. The term "immersion" as used herein does not mean that a structure, such as a substrate, must be submerged in liquid, but rather means that liquid is located between the projection system and the substrate during exposure.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD comprising, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may comprise an adjuster AD for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may comprise various other components, such as an integrator IN and a condenser CO. The illuminator may be used to condition the radiation beam, to have a desired uniformity and intensity distribution in its cross-section.

The radiation beam B is incident on the patterning device (e.g., mask MA), which is held on the support structure (e.g., mask table MT), and is patterned by the patterning device. Having traversed the mask MA, the radiation beam B passes through the projection system PS, which focuses the beam onto a target portion C of the substrate W. With the aid of the second positioner PW and position sensor IF (e.g. an interferometric device, linear encoder or capacitive sensor), the substrate table WT can be moved accurately, e.g. so as to position different target portions C in the path of the radiation beam B. Similarly, the first positioner PM and another position sensor (which is not explicitly depicted in FIG. 1) can be used to accurately position the mask MA with respect to the path of the radiation beam B, e.g. after mechanical retrieval from a mask library, or during a scan. In general, movement of the mask table MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the mask table MT may be connected to a short-stroke actuator only, or may be fixed. Mask MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the mask MA, the mask alignment marks may be located between the dies.

The depicted apparatus could be used in at least one of the following modes:

1. In step mode, the mask table MT and the substrate table WT are kept essentially stationary, while an entire pattern imparted to the radiation beam is projected onto a target portion C at one time (i.e. a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the mask table MT and the substrate table WT are scanned synchronously while a pattern imparted to the radiation beam is projected onto a target portion C (i.e. a single dynamic exposure). The velocity and direction of the substrate table WT relative to the mask table MT may be determined by the (de-)magnification and image reversal characteristics of the projection system PS. In scan mode, the maximum size of the exposure field limits the width (in the non-scanning direction) of the target portion in a single dynamic exposure, whereas the length of the scanning motion determines the height (in the scanning direction) of the target portion.

3. In another mode, the mask table MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

A number of sensors is used at substrate level for evaluating and optimizing imaging performance. These may include transmission images sensors (TIS, not shown), spot sensors (not shown) for measuring exposure radiation dose and integrated lens interferometers (ILIAS, not shown).

The transmission image sensor is used to determine the positions of a reticle (MA) and a substrate (W) relative to each other in six degrees of freedom (three in translation and three in rotation). The reticle (MA) comprises a reticle mark ($M_1$). An image of the reticle mark ($M_1$) is formed by the projection system (PS) onto the transmission image sensor placed in a substrate table (WT), the image formed using a radiation beam (B).

Figure 2:
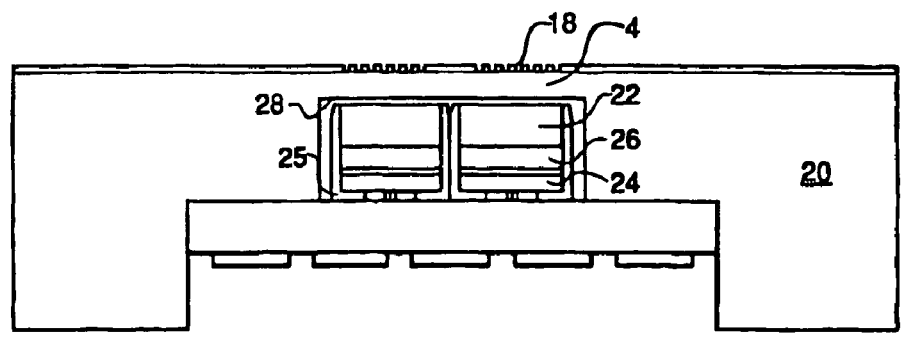
FIG. 2 illustrates a side view of a sensor according to one embodiment of the invention.

The transmission image sensor is shown in FIG. 2. The transmission image sensor comprises a grating structure (18) with transmissive and reflective (or absorbing) elements (for instance a transmissive pattern in a layer of chromium). When the image (not shown) of the reticle mark (not shown) is in focus at, and aligned with the grating structure (18), the transmissive elements correspond to the image. A detector (24), such as a photodiode, is positioned behind the grating structure (18), the detector (24) being constructed to measure the intensity of the radiation behind the grating structure (18).

If the image is in focus at, and aligned with the grating structure (18), all radiation passes through the grating structure (18), resulting in a maximal intensity at the detector (24). If the image is not in focus at the grating structure (18) or is misaligned with the grating structure (18), part of the radiation falls onto the reflective (or absorbing) elements and the intensity measured by the detector (24) behind the grating structure (18) will be lower.

At several relative positions between the reticle (not shown) and the substrate table (not shown) intensities of radiation that have passed the reticle mark (not shown) and the grating structure (18) are measured by the detector (24) to find the position where the measured intensity is maximal. This relative position corresponds with the reticle mark being in focus at and aligned with the grating structure (18) of the transmission image sensor.

Alternative embodiments may be possible as will be explained using FIG. 1. For instance a mark may be provided on the mask table (MT) or on a fiducial part (not shown) on the mask table (MT) in order to align the mask table (MT), rather than the reticle (MA), to the substrate table (WT).

To determine rotation of the reticle (MA) relative to the substrate table (WT), several marks may be present on the reticle (MA) or on the mask table (MT) or several fiducial parts may be present on the mask table (MT) and several grating structures may be present on the substrate table (WT) as well.

According to another embodiment, several marks may be present on the reticle (MA) or on the mask table (MT) or several fiducial parts may be present on the mask table (MT) to qualify the projection system (PS). This may be done, for instance, by determining the magnification of the projection system (PS) by measuring the positions of the images of several reticle marks ($M_1, M_2$) on the reticle (MA) one by one using the grating structure (not shown) and the detector (not shown) and comparing the distance between the measured positions with the distance of the several marks ($M_1, M_2$) on the reticle (MA). Alternatively, the scaling of the projection system (PS) can be measured. Different illumination settings are used in combination with different projected images for measuring properties such as pupil shape, coma, spherical aberration, astigmatism and field curvature.

The detailed configuration of each of the elements of FIG. 2 depends on the properties of the radiation to be detected.

In FIG. 2, the grating structure (18) may be supported on top of a quartz sensor body (20), i.e. on the same side of the body as the projection system. The transmission image sensor is preferably capable of measuring the influences of all illumination settings (sigma, lens NA, all masks (binary, PSM, etc.)) so that a small line width of the grating structure (18) is preferable.

The detector (24), in contrast, may be arranged within the sensor body (20), or within a concave region formed on the side of the sensor body (20) facing away from the projection system (not shown).

The example of the transmission image sensor of FIG. 2 is for use with DUV radiation. The grating structure (18) is realized using e-beam lithography and dry etching techniques in a thin layer of chromium deposited on a substrate using sputtering. Any DUV light that is projected towards the transmissive elements in the grating structure (18) is transmitted by a transmissive plate (4) which may be quartz or fused silica and hits the underlying luminescent material (22), or "phosphor". The luminescent material (22) may consist of a slab of crystalline material that is doped with rare-earth ions, e.g. yttrium-aluminium-garnet doped with cerium (YAG:Ce). The main purpose of the luminescent material (22) is to convert the DUV radiation into more easily detectable visible radiation, which is then detected by the detector (24), e.g. a photodiode. DUV radiation that has not been absorbed and converted into visible radiation by the phosphor (22) may be filtered out before it reaches the detector (24), e.g. by a BG-39 or UG filter (26). Without the use of an index matching fluid in the transmission image sensor, air may be present in the gaps between a rear side (28) of the transmissive plate (4) and the luminescent material (22). The lumeniscent material (22), the filter (26) and the detector (24) are mounted in a sensor housing (25). Air may be present in the gaps of components mounted in the sensor housing (25). The presence of air yields a number of air/material/air interfaces that interrupt the propagation of radiation.

At boundaries between media of different refractive indices a proportion of incident radiation will be reflected and potentially lost from the sensor. For optically smooth surfaces, the extent to which this occurs depends on the angle of incidence of the radiation and the difference in refractive index of the media in question. For radiation incident at and above a "critical angle" (conventionally measured from normal incidence) total internal reflection may occur, leading to serious loss of signal to later elements of the sensor. This may be a particular problem in high NA systems where radiation may have a higher average angle of incidence. Several arrangements are possible whereby air is excluded from the region between the grating structure (18) and detector (24) in order to avoid interfaces between media of high refractive index and air.

In addition to losses due to partial and total internal reflection, absorption may also seriously reduce the intensity of radiation reaching the photocell, as may scattering from interfaces that are not optically smooth.

A substantial contribution to the reduced sensitivity of the prior art arrangements is loss of radiation from the sensor before it even reaches the final element of the radiation-detecting element. As discussed above, radiation may be lost due to scattering from rough surfaces or via total or partial internal reflection at interfaces within the detector. Alternatively, air gaps containing oxygen and water may lead to substantial absorption of radiation passing through.

By considering the path of DUV radiation and radiation arising from luminescence, regions may be identified where radiation is likely to be lost in the arrangement described above and illustrated in FIG. 2.

The first region of interest is the rear-side (28) of the transmissive plate (4), reached by DUV radiation after it has passed through the grating structure (18) and transmissive plate (4). Here, the surface has been formed mechanically, such as by drilling, and is inevitably rough on the scale of the wavelength of the radiation. Radiation may therefore be lost due to scattering, either back into the transmissive plate (4) or out past the luminescent material (22). Secondly, after this interface, the DUV light encounters the optically smooth air/YAG:Ce interface, where a substantial amount of reflection may occur due to the refractive index mismatch, particularly in systems of high NA. Thirdly, the luminescent material (22) emits radiation in random directions. Due to its relatively high refractive index, the critical angle for total internal reflection at the YAG:Ce/air boundary is around 33° (there is air in the gap between the YAG:Ce and the filter) from the normal, such that a large proportion of radiation incident on the boundary is reflected out of the luminescent material (22) to the sensor housing (25), through the side walls of the luminescent material (22). Finally, the part of the luminescence that is directed towards the detector (24) overcomes the air/quartz interface on the detector surface where surface roughness may again account for loss of detected signal.

Figure 3:
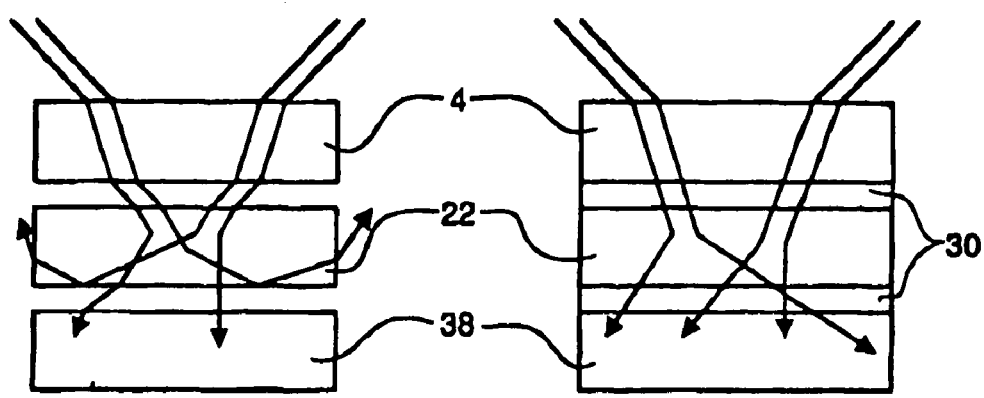
FIG. 3 illustrates a schematic arrangement of several members of a DUV sensor according to one embodiment of the invention.

FIG. 3 illustrates a schematic arrangement that addresses the problems described above as well as exemplary radiation ray paths. Filler sheets 30, which may be made from light transmitting plastics, are inserted between components to reduce the effect of radiation scattering at air/material interfaces with high surface roughness or large refractive index discontinuities. For example, the filler sheets 30 may be arranged to be transmissive for either DUV radiation, visible radiation, or both. Additionally, the refractive index of each filler sheet 30 may be tuned to provide the most efficient refractive index matching between media with which it is in contact.

The filler sheet (30) may be arranged to have a refractive index equal to or greater than the refractive index of the immersion liquid (not shown) present above the transmissive plate (4). In the typical case where the relevant interfaces (immersion liquid to transmissive plate and transmissive plate to filler sheet) are parallel to each other and perpendicular to the axis of the projection system, this condition ensures that no internal reflection will occur at the transmissive plate (4) to filler sheet (30) interface. If the interfaces were made non-parallel, then a corresponding increase in the lower refractive index bound for the filler sheet 30 may be chosen.

According to one embodiment for filler sheets 30, a DUV sensor may include a transmissive plate 4, luminescent material 22 and a detector, such as a photodiode 38 illustrated in FIG. 3. The right-hand diagram comprises filler sheets 30 while, for comparison, the left-hand diagram does not. In each case, arrows show exemplary ray paths through the stack, with internal reflection occurring at the YAG:Ce/diode interface when the filler sheets are absent.

One or more of the optical components (e.g. transmissive plate, filler sheet and/or luminescence layer) of the sensor at substrate level may include an internal-reflection-enhancing layer on its outer lateral surface. This layer may be constructed by roughening the outer surface and/or applying a metallic layer to it. This feature acts to reflect radiation back into the sensor that would otherwise have been lost.

Light transmitting plastics may deteriorate in use because of the highly energetic DUV radiation transmitted by the plastics. Where a filler sheet 30 is in contact with an optically rough surface, some deformation of the filler sheet 30 may be necessary to ensure that it closely follows the surface roughness and does not leave any tiny air pockets. This may be achieved by mechanically compressing the filler sheet 30 onto the surface in question. Compressing the filler sheet may be damaging to the part comprising the surface in question. Alternatively, the filler sheet 30 may be heated until it flows sufficiently to follow the surface roughness. This may be damaging to the sensor as well because of excessive oxidation or other chemical decomposition that may occur at high temperature. Finally, due to production tolerances, the air gaps of two sensors that are produced using the same specifications, in practice do not have equal heights. Therefore, it may occur that the filler sheet, produced in advance at a certain height (i.e. with a certain thickness), does not fill the complete air gap, so that still radiation is lost.

It is also possible to use fluids as filler layers, chosen to have as high a refractive index as possible, for example Fomblin. Liquids automatically follow rough surfaces without the need for heating or compressing. Variations in the height of the filler sheet (30) can be accounted for by varying the amount of applied liquid.

It is advantageous to ensure the liquid is kept at its intended position because the transmission image sensor is typically mounted on a substrate support table that moves at high speed, for instance, while stepping to bring a second target portion below the projection system, after the first target portion has been irradiated. Without proper containment of the liquid, the liquid would flow away from its desired place during such a movement.

Because of the production tolerances leading to variations in the height of the filler sheets (30), seals designed to contain the liquid in the filler sheets may account for these variations. Therefore, the use of flexible seals may be used. However, flexible seals may include molecules that gas out. Having these kinds of molecules gassing out in a lithographic apparatus may cause undesired contamination of the machine and therefore may not be used in practice. Also, seals may transfer forces from the transmissive plate (4) to the luminescence material (22) or from the luminescence material (22) and the photodiode (38). Such a transfer of forces may be undesirable.

Figure 4:
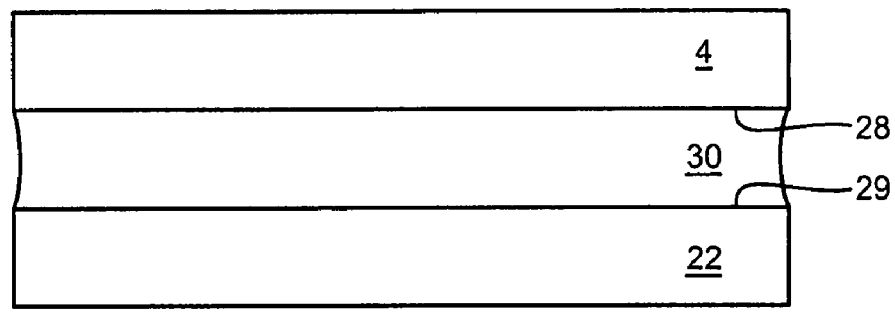
FIG. 4 illustrates a side view of the first and second member according to one embodiment of the invention.

According to one embodiment of the invention illustrated in FIG. 4, liquid (30) is applied between the rear-side of the transmissive plate (4) and the luminescent material (22). The rear-side of the transmissive plate (4) forms a first surface (28) and the side of the luminescent material (22) that faces the first surface (28) forms a second surface (29). The first surface (28) and the second surface (29) form a set of opposing surfaces. The first surface (28) and the second surface (29) are placed closely together, so that the liquid (30) is contained by capillary forces exerted by the first surface (28) and the second surface (29). This is because the closer the distance between the first surface (28) and the second surface (29), the less mass of liquid is contained between those surfaces. In case the sensor accelerates in a direction parallel to the first surface, i.e. sideways, the forces pulling on the liquid will have a linear relationship with the mass of the liquid. Such an acceleration is frequently present in sensors comprised in a substrate table (not shown) of a lithographic apparatus. The capillary forces are applied to contain the liquid (30) even if the sensor is accelerated as described. Thus, the smaller the distance between the first surface (28) and the second surface (29), the greater the capillary forces are to contain the liquid (30).

It is obvious that in an analogue way, the luminescent material (22) and the photodiode (38) could form a first surface (28) and a second surface (29) and could be arranged to exert capillary forces on liquid (30) between those surfaces.

In an embodiment of the invention, Fomblin is chosen as the liquid to be used. Other liquids can be used as well, such as other liquids from the group of tetrafluoroetylens and water. The distance in the area where the liquid is fixed is chosen depending on the choice of liquid and the surface conditions of the first and second surfaces. According to one embodiment, the distance may be between 1 and 0.001 mm.

Figure 5:
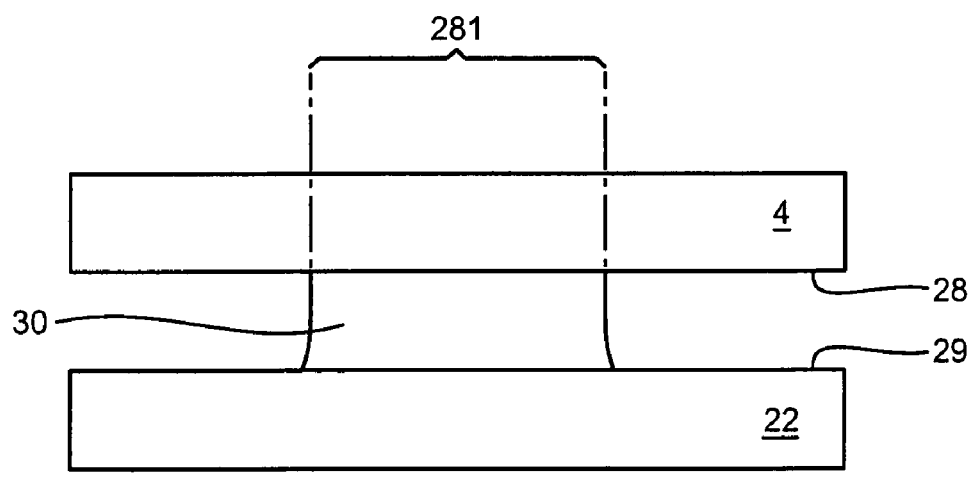
FIG. 5 illustrates a side view of the first and second member according to one embodiment of the invention.

During regular production, the liquid (30) may be supplied to fill only a part of the space between the first surface (28) and the second surface (29), as shown in FIG. 5. A preferential position for the liquid (30) will be created when the first surface (28) of the transmissive plate (4) is arranged to exert the capillary forces via predetermined first area (281) of the first surface (28). In FIG. 5, a side view is shown, wherein the liquid (30) has a position corresponding to the first area (281) and wherein the first area (281) is circularly symmetrical. The liquid (30) corresponding to the first area will be contained between the first surface (28) and the second surface (29) of the luminescent material (22) by those capillary forces, whereas liquid that would be in a position that would not correspond to the first area (281) would not be contained by the capillary forces.

Figure 6:
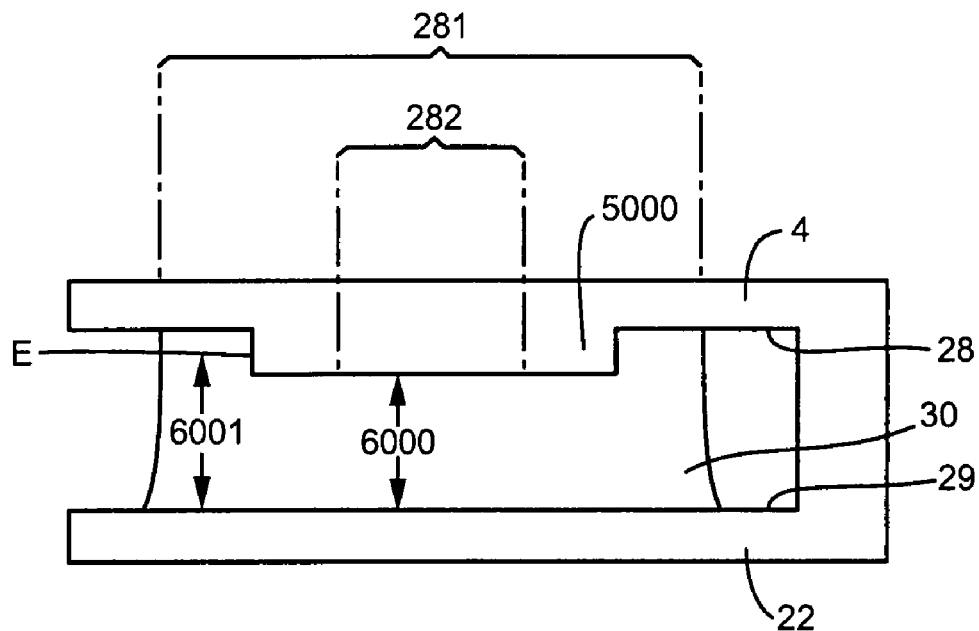
FIG. 6 illustrates a side view of the first member having a protrusion according to one embodiment of the invention.

FIG. 6 shows a side view of an example of a sensor applying the invention. In this example, the first surface (28) of the transmissive plate (4) has a protrusion (5000) in the first area (281). The protrusion (5000) protrudes towards the second surface (29) and is circularly symmetrical. By protruding towards the second surface (29) of the luminescent material (22), the distance between the first surface (28) and the second surface (29) is decreased, thereby decreasing the mass of the liquid contained by the capillary forces. This can clearly be seen for the liquid (30) making contact with a protrusion area (282) of the protrusion (5000). The distance (6000) between the protrusion area (282) and the second surface (29) is smaller than the distance (6001) between the first surface (28) and the second surface (29) outside the protrusion.

Figure 7:
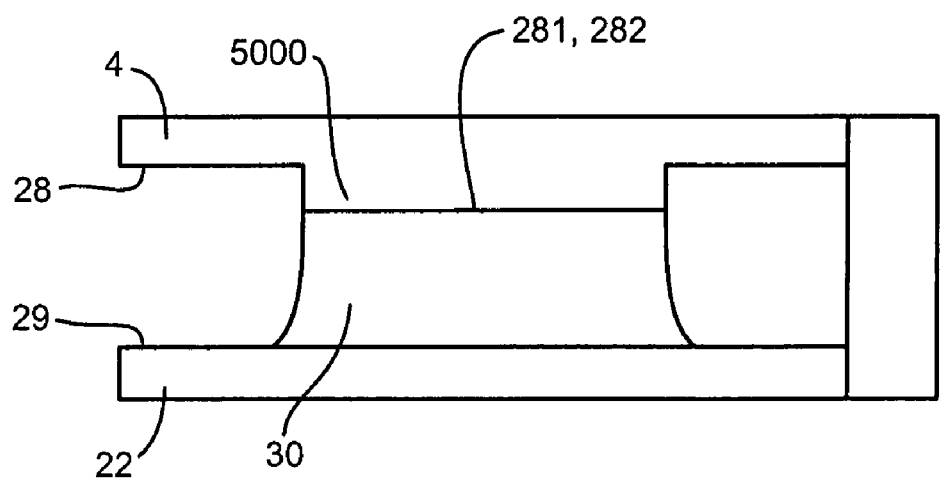
FIG. 7 illustrates a side view of the first member having a protrusion according to one embodiment of the invention.

FIG. 7 shows a side view of another example of a sensor according to the invention. In this example, the protrusion area (282) is identical to the first area (281), so that the liquid (30) between the first surface (28) of the transmissive plate (4) and second surface (29) of the luminescent material (22) experiences capillary forces whenever present between the protrusion (5000) and the second surface (29). In other words, the position of the protrusion (5000) along the first surface (28) determines where the capillary forces area exerted on the liquid (30). Again, the first area (281) is circularly symmetrical.

In FIG. 7, the distance between the first surface (28) and the second surface (29) is constant throughout the protrusion area. Therefore, within the protrusion area (282) itself, the liquid (30) has no preferred position. A way to reach such a constant distance, the protrusion area (282) may substantially be flat. By having a substantially flat second surface (29) as well, the distance is constant throughout the protrusion area (282) if the protrusion area (282) and the second surface (29) are parallel. Substantially flat surfaces are relatively easily obtained by polishing. Parallel positioning is relatively easily obtained by guide poles (not shown) through holes in both the transmissive plate (4) and the luminescent material (22).

Figure 8:
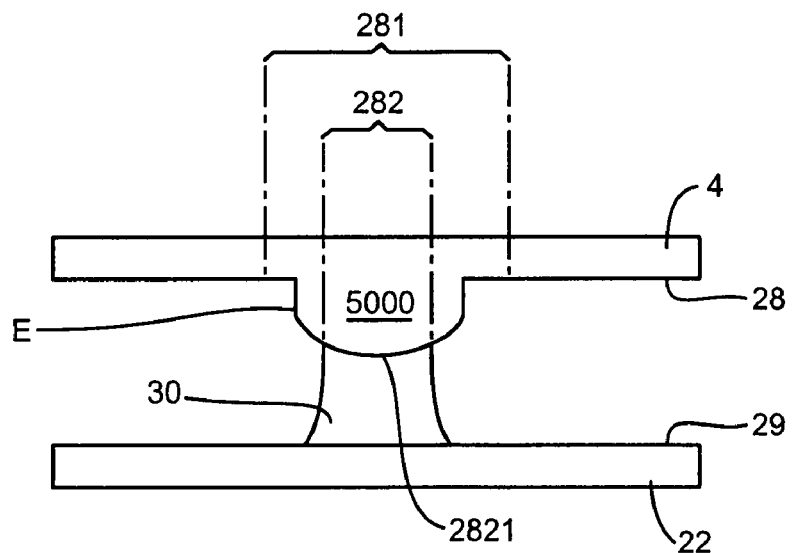
FIG. 8 illustrates a side view of the first member having a curved protrusion according to one embodiment of the invention.

A sensor according to the invention may have a protrusion (5000) with a circular boundary (E). This is shown in FIG. 8, which shows a cross section of a transmissive plate (4) with a first surface (28) having a first area (281) and a luminescent material (22) with a second surface (29) in side view. The first area (281) has a protrusion (5000) having a surface with a curvature facing the second surface (29). The curvature is such that in the middle (2821) of the protrusion (5000), the distance from the protrusion (5000) to the second surface (29) is smaller than at the boundary (E). Since the capillary forces can contain water (30) better if the distance between the surfaces is smaller, this means that at the middle (2821) of the protrusion (5000) the water (30) is better contained than at the edge. This gives a preferential position for the water (30) at the protrusion (5000). On the other hand, since the protrusion area (282) is curved, optical radiation passing from the transmissive plate (4) via the first surface (28) to the water, experiences refraction. This refraction may be used to condition the radiation.

The protrusion area (282) does not extend to the boundary (E). Any position inside the protrusion (5000), will therefore be at a distance from the boundary (E), in other words, away from the boundary (E). Because of the curvature, at any position inside the protrusion (5000) the distance between the protrusion area (282) and the second surface (29) will be smaller than the distance between the protrusion (5000) and the second surface (29) at the boundary (E) of the protrusion.

It will be obvious that the boundary need not be circular, but may also be square, rectangular etc.

Figure 9:
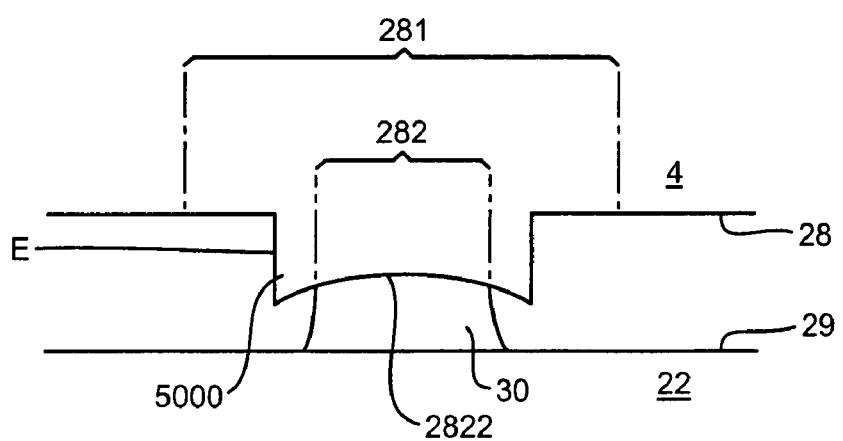
FIG. 9 illustrates a side view of the first member having a curved protrusion according to one embodiment of the invention.

The protrusion (5000) may also have a curvature such that in the middle (2822) of the protrusion (5000) the distance from the protrusion (5000) to the second surface (29) is larger than at the boundary (E). This is shown in FIG. 9, wherein the sensor comprises a transmissive plate (4) having a first surface (28) with a first area (281) and comprises a luminescent material (22) with a second surface (29). The protrusion (5000) is in the first area (281) and has a protrusion area (282). The middle (2822) of the protrusion (5000) is in the protrusion area (282). Curvature of the protrusion (5000) may be used to refract radiation passing through the protrusion (5000).

It will be understood that if the protrusion area (282) does not extend to the boundary (E) at every position in the protrusion area (282), the distance to the second surface (29) will be smaller than the distance form the protrusion (5000) at the boundary (E) to the second surface (29). Because every position in the protrusion area (282) is away from the boundary (E) and because of the curvature at every position in the protrusion area (282), the distance between the protrusion area (282) and the second surface (29) is larger than the distance between the protrusion (5000) and the second surface (29) at the boundary (E) of the protrusion. This means that at the boundary (E) the capillary forces have an improved capability to contain the water (30) in comparison to the capillary forces at every position in the protrusion area (282). The further away from the middle of the protrusion (5000), the better the capillary forces will be capable of preventing the water (30) flowing away from the protrusion.

Figure 10:
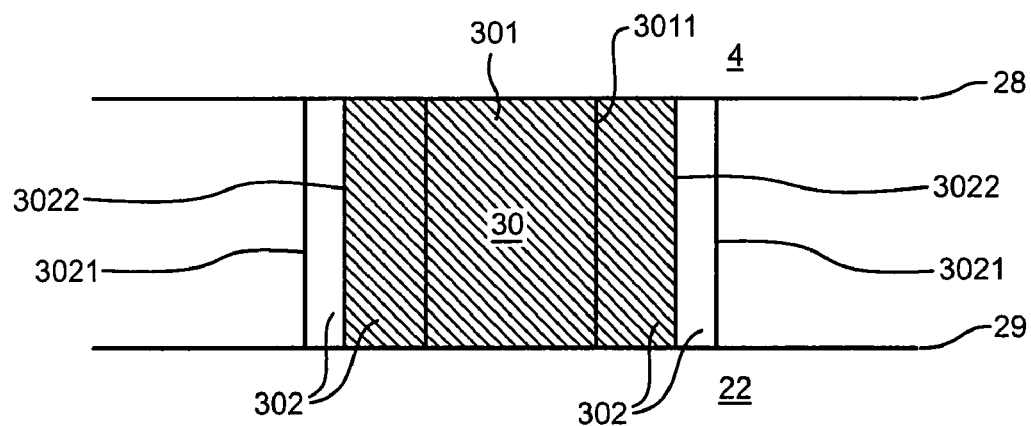
FIG. 10 illustrates a side view of the liquid in the optical volume and the overflow volume according to one embodiment of the invention.

In a sensor according to the invention, the sensor comprises an amount of liquid (30), such as water, which does not completely fill the space between the first surface (28) of the transmissive plate (4) and the second surface (29) of the luminescent material (22). This is shown in FIG. 10. The sensor is arranged to transmit optical radiation to be measured via an optical volume (301) at a predetermined position between the first surface (28) and the second surface (29). While the complete space between the first surface (28) and the second surface (29) is not filled with liquid (30), in the optimal situation, the complete optical volume (301) is filled by the liquid (30) to prevent optical losses for the reasons as explained earlier. The rest of the liquid (30) is in an overflow volume (302). The overflow volume (302) and the optical volume (301) make contact through an imaginary first connection area (3011) which forms an outer perimeter of the optical volume (301). The overflow volume (302) is defined by the first surface (28) and the second surface (29) and has an outer perimeter (3021). The first connection area (3011) and the outer perimeter (3021) of the overflow volume have a cylindrical shape. Therefore, the optical volume (301) has a circularly symmetrical disk shape and the overflow volume has a ring shape. In the overflow volume (302), the capillary forces are lower than in the optical volume (301). The volume of liquid (30) may not be sufficient to fill both the optical volume (301) and the overflow volume (302) at the same time. Therefore, a part (3022) of the overflow volume (302) does not comprise liquid (30). The liquid (30) preferentially resides in the optical volume (301) and not in the overflow volume (302), since the capillary forces are larger in the optical volume (301) than in the overflow volume (302). In other words, if the liquid (30) would have filled the overflow volume (302) completely and the optical volume (301) only partly, then the liquid (30) would flow from the overflow volume (302) through the first connection area (3011) to the optical volume (301) until the optical volume (301) was completely filled. When the optical volume (301) is completely filled again, there is no liquid (30) flowing from the overflow volume (302) to the optical volume (301) and a stable situation would be reached.

One of ordinary skill will understand that the optical volume (301) and the overflow volume could have any desired shape. For instance the optical volume can be rectangular or square when viewed from the first surface (28).

Figure 11:
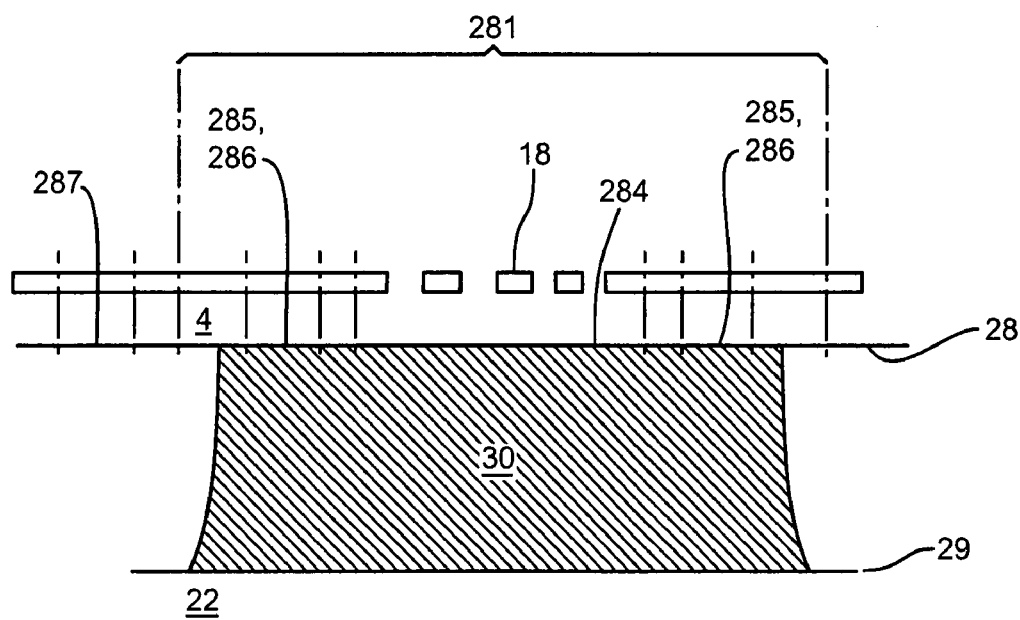
FIG. 11 illustrates a side view of the first member having an optical area and the second member according to one embodiment of the invention.

An embodiment of the invention with additional advantages is shown in FIG. 11. FIG. 11 shows a transmissive plate (4) having a first surface (28) and a luminescent material (22) having a second surface (29). The transmissive plate (4) and the luminescent material (22) are a first and a second member of a sensor useable in a lithographic apparatus. The sensor is arranged to exert the capillary forces on a liquid (30) via a first area (281) of the first area (28). The sensor comprises a grating structure (18) positioned so as to transmit optical radiation via an optical area (284) of the first surface (28). Outside the optical area (284) no optical radiation impinges on the first surface (28). The optical area is circularly symmetrical. To increase the effect of the capillary forces, the first area (281) further comprises a barrier area (285) which forms a ring surrounding the optical area (284). The barrier area (285) exerts higher capillary forces on the liquid (30) than the optical area (30). The capillary forces exerted by barrier area (285) are high enough to contain the liquid (30), even when the sensor is accelerated parallel to the first surface (28), i.e. sideways. This means that the capillary forces exerted by the optical area (284) are not necessary to contain the liquid (30) during acceleration. The optical area (284) is optimized for optical performance. For instance, the optical area (285) is treated with an anti-reflex coating (not shown). Also, the optical performance may be better if the distance between the optical area (284) and the second surface is relatively large in comparison to the distance at the barrier area (285) (not shown). On the other hand, since no radiation is transferred via the barrier area, the barrier area does not need to comply with optical requirements. The barrier area can be optimized to exert capillary forces. For instance, it may be positioned at a very small distance to the second surface (29). Also, the barrier area may be treated with a hydrophilic coating in a first treatment area (286). A hydrophilic coating in a first treatment area (286) in the barrier area (285) increases the forces containing water as the liquid (30). It will be understood, that alternatively the hydrophilic coating could be applied on the second opposing surface, i.e. on the luminescent material (22) or on both opposing surfaces.

Alternatively, a second treatment area (287) outside the first area (281), is provided with a hydrophobic coating. A hydrophobic coating repels water. The first area (281) is not provided with a hydrophobic coating. Therefore, by using water as the liquid (30), the forces containing the liquid (30) are higher in the first area (281) than in the second treatment area (287). Since in this example, the optical area is in the first area (281) and not in the second treatment area (287), no optical radiation will pass the hydrophobic coating. This has the advantage that there is a wide choice of hydrophobic coatings available, since the coating does not have to fulfill optical requirements. Alternatively, both a hydrophobic coating and a hydrophilic coating are applied in combination on at least one of the opposing surfaces.

Alternative surface treatments to repel or attract the liquid (30) are possible as well. For instance, a change in surface roughness may be applied.

Figure 12:
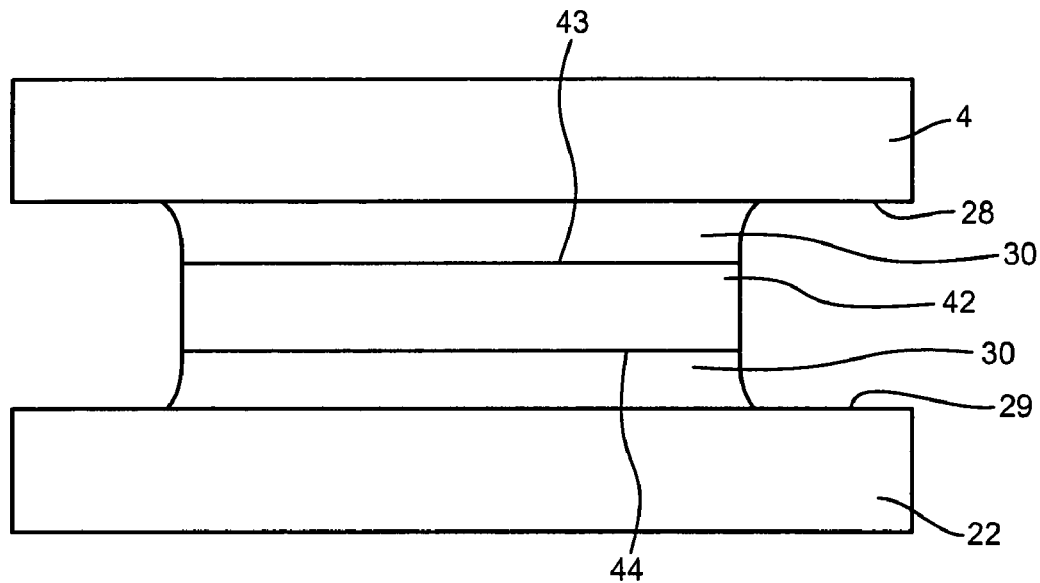
FIG. 12 illustrates a side view of a sensor having an intermediate plate according to one embodiment of the invention.

An alternative embodiment of the invention is shown in FIG. 12. A sensor comprises a transmissive plate (4) having a first surface (28) (the rear-side) and a luminescent material (22) comprising a second surface (29). The sensor comprises a liquid (30). The first surface (28) and the second surface (29) are at a distance such that for expected accelerations parallel to the first surface (28), the liquid (30) is expected to flow away. To overcome this, an intermediate plate (42) is inserted between the first surface and the luminescent material (22). The intermediate plate (42) comprises a third surface (43) facing the first surface (28). The surface on the intermediate plate (42) facing the second surface (29) forms a fourth surface (44). A liquid (30), for instance water, is contained, between the first surface (28) and second surface (29) i.e. the position of the water is fixed, by capillary forces. The capillary forces on the liquid (30) between the transmissive plate (4) and the intermediate plate (42) are exerted by the first surface (28) and the third surface (43). The capillary forces on the liquid (30) between intermediate plate (42) and the luminescent material (22) are exerted by the second surface (29) and the fourth surface (44). Thus, the total capillary forces on the material between the first surface (28) and the second surface (29) are increased by the capillary forces exerted by the third surface (43) and the fourth surface (44). Therefore, the capillary forces can contain more material between the first surface (28) and the second material (29) than without the presence of the intermediate plate (42). The specific weight of the material of the intermediate plate (42) is lower than the specific mass of the liquid (30), so that the total mass of the material to be contained by the capillary forces is decreased. This creates additional leverage of the capillary forces over acceleration forces parallel to the first surface (28).

In an embodiment, the intermediate plate (42) is replaced by an intermediate part (not shown) having a curved third surface (43) facing the first surface (28) and a curved forth surface (44) facing the second surface (29) so that it functions as a positive lens. Alternatively, the intermediate plate (42) has a recess at the edge.

Figure 13:
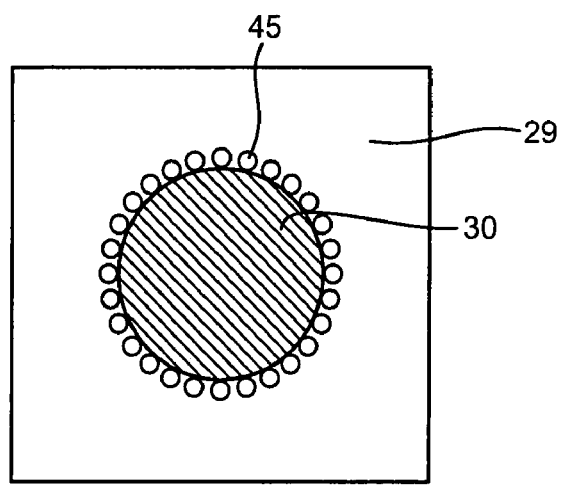
FIG. 13 illustrates a cross section of a sensor having intermediate bodies according to one embodiment of the invention.

In an embodiment of the invention, shown in FIG. 13, the distance between the first surface (28, not shown) and the second surface (29) is too large to contain the liquid (30) by capillary forces exerted between the first surface (28) and the second surface (29) themselves. Spherical, intermediate bodies (45) are inserted between the first surface (not shown) and the second surface (29). FIG. 13 shows a top view of the spherical, intermediate bodies (45) as seen from the first surface (28). The spherical, intermediate bodies (45) form a circle. Between the spherical, intermediate bodies (45) there is a small space. Alternatively the spherical, intermediate bodies (45) are in contact with each other. The space between the rear-side (28) of the transmissive plate (4) and the luminescent material (22) and inside the circle is filled with water (30). The space between the spherical, intermediate bodies (45) is so small that the water (30) entering the space between the spherical, intermediate bodies (45), is contained in that space by capillary forces. The space formed between the spherical, intermediate bodies (45) and each of the first surface (28) and the second surface (29) comprises the water (30) by capillary forces in the same way. Alternatively, the intermediate bodies (45) may have different shapes than spherical shapes, such as a cylindrical shape. Alternatively an additional intermediate bodie (46) is present in the area formed by the circle as well. This has the advantage, that additional force must be exerted on the water (30) before it will flow through the intermediate bodies (45) at the edge of the circle. The additional spherical, intermediate bodies (46) within the circle cause capillary forces between the bodies and the first surface (28) and the second surface (29) in the same way as the intermediate bodies (45) at the edge of the circle. Alternatively, the intermediate bodies (45) are not placed in a circle but on a closed contour with an arbitrary shape. The sensor is arranged to transmit optical radiation to be measured via an optical area (284). The arbitrary shape is chosen so that it comprises the complete optical area (284).

Figure 14:
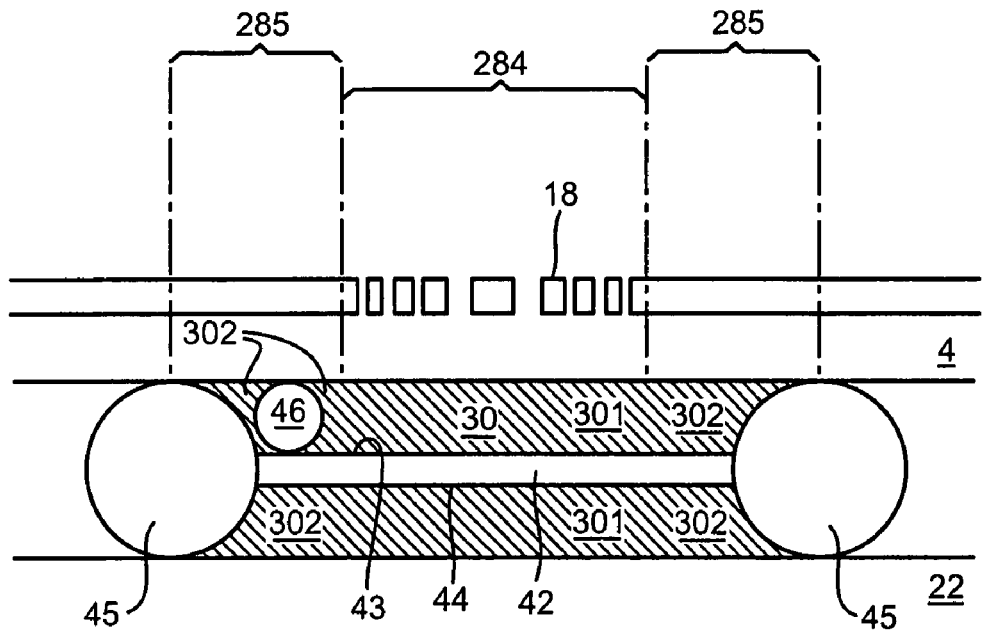
FIG. 14 illustrates a side view of a sensor having an intermediate plate and intermediate bodies according to one embodiment of the invention.

Alternatively, the intermediate bodies (45) and the additional intermediate bodies (46) are used in combination with the intermediate plate (42). This is shown in FIG. 14. Having the intermediate bodies (45) between the first surface (28) of the transmissive plate (4) and second surface of the luminiscent material (22) and besides the intermediate plate (42) increases the working of the capillary forces. Water (30) on the edge of the intermediate plate (42) also experiences the capillary force of the intermediate bodies (45), fixing the position of the water (30). For example, the intermediate plate (42) is a disk, and the intermediate bodies (45) form a circle around the intermediate plate (42), whereby the intermediate bodies (45) are spheres. The intermediate bodies (45) are positioned very close to each other so that liquid (30) in the space between the intermediate bodies (45) is kept in place by capillary forces. One or more additional intermediate bodies (46), for instance spheres, reside between the rear-side (28) of the transmissive plate (4) and the intermediate plate (42). Alternatively, one or more additional intermediate bodies (46) reside between the fourth surface (44) of the intermediate body (42) facing the second surface (29) and the second surface (29). Alternatively, one or more additional intermediate bodies (46) reside between the first surface (28) and the third surface, and one or more additional intermediate bodies (46) reside between the fourth surface (44) and the second surface (22).

In FIG. 14, the optical area (284) corresponds to an optical volume (301) and the barrier area (285) corresponds to an overflow volume (302). The sensor comprises a grating structure (18) so that optical radiation to be measured is only transmitted via the optical area (284) and the optical volume (301). The additional intermediate bodies (46) are not transparent to the optical radiation to be measured. This is not a problem, since the one or more additional intermediate bodies (46) area in the overflow volume (302). Optical radiation to be measured only passes the optical volume (301) and therefore is not influenced by the additional intermediate bodies (46). Still, the one or more additional intermediate bodies (46) increase the capillary forces on the water (30).

Additionally, in the transmission sensor of FIG. 2, a non flexible, leak tight seal may be mounted between the sensor housing (25) and the walls of the quartz sensor body (20) perpendicular to the transmissive plate (4). Between those walls, there may be much more room than between the lumeniscent material (22) and the rear-side (28) of the transmissive plate. Also, the tolerances in this direction may be much lower. This is because the position of the surface of the luminescent material (22) facing the rear-side (28) of the transmissive plate, depends on several tolerances, such as the production and placement tolerances of the sensor housing (25), the production and placement tolerances of the luminescent material (22). The tolerance between the sensor housing (25) and the walls of the quartz sensor body (20) perpendicular to the transmissive plate (4) depends on the production and placement tolerance of the sensor housing (25) alone. Thus, a non flexible leak tight seal can be applied. It may be desirable to have a seal, because liquid may vaporize or gas out. This would then leave the sensor without filler sheet, so that it would not be fit for use with high NA radiation anymore. Also, in a lithographic machine, the gasses must be very pure. Vapor from a liquid inside a sensor may cause deterioration of some processes or components in the machine. For instance, a non flexible leak tight seal could be applied that does not fill the complete opening between the sensor housing (25) and the walls of the quartz sensor body (20). Thereby, the opening is reduced considerable and the vaporization can be brought to an acceptable level. It must be noted, that vaporization of the liquid can be acceptable to a larger extend than gassing out of molecules of the flexible seal.

It will be appreciated that although embodiments above are described with the liquid fixed between the rear-side of the transmissive plate (4; FIG. 2) and the luminescent material (22; FIG. 2), the present invention could be embodied with the liquid fixed in other positions as well, such as between the luminescent layer (22; FIG. 3) and the detector (38; FIG. 3).

Figure 15:
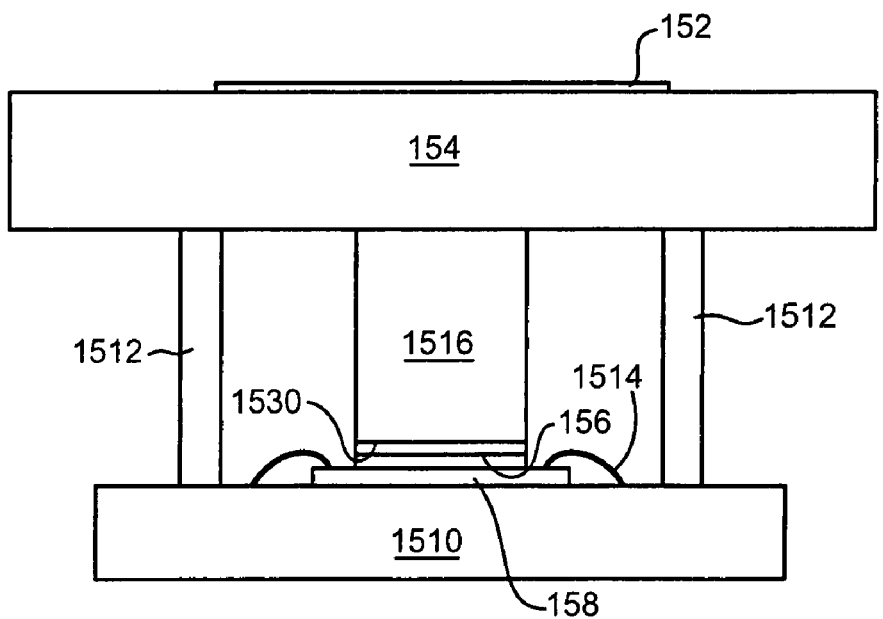
FIG. 15 illustrates a side view of a sensor module of a wavefront sensor according to one embodiment of the invention.

An embodiment of the invention comprises an integrated lens interferometer which is used to measure lens aberrations of a projection system of a lithographic apparatus per field point. The integrated lens interferometer is a wavefront sensor which is based on the principle of shearing interferometry and comprises a source module and a sensor module. The source module has a patterned layer of chromium that is placed in the object plane of the projection system and has additional optics provided above the chromium layer. The source module provides a wavefront of radiation to the entire pupil of the projection system. The sensor module is shown in FIG. 15 and has a patterned layer 152 of chromium that is placed in the image plane of the projection system (not shown). The patterned layer 152 of chromium is supported by a transmissive plate 154, in this case glass. Alternatively the transmissive plate 154 can be made from quartz. A quantum conversion layer 156 may be positioned immediately above a camera chip 158, the camera chip being a radiation-detecting element. The camera chip (158 is mounted on a substrate 1510 at some distance behind said patterned layer 152 of chromium. The substrate 1510 is connected to the transmissive plate 154 via spacers 1512. Bonding wires 1514 connect the radiation-detecting element to external instrumentation. Alternatively, the radiation-detecting element is connected to external instrumentation via bumps. The patterned layer of chromium on the sensor module diffracts radiation into several diffraction orders that interfere with each other giving rise to a interferogram. The interferogram is measured by the camera chip 158. The aberrations in the projection lens can be determined by software based upon the measured interferogram.

A filler sheet 1516 of the same material as the transmissive plate 154, or of similar optical properties, is inserted between the transmissive plate 154 and the quantum conversion layer 156. A small gap is left between the filler sheet 1516 and the quantum conversion layer 156. The small gap contains Fomblin 1530. Alternatively, other liquids may be used, such as water. The advantage of this embodiment is that no radiation will be absorbed. At the same time, the gap between the filler sheet 1516 and the quantum conversion layer 156 ensures that the filler sheet 1516 does not place excessive pressure on the quantum conversion layer 156 and thereby on the camera chip 158 due to production tolerances. Too much pressure on the quantum conversion layer 156 and thereby on the camera chip 158 disturbs the measurement. This pressure would be present if the filler sheet 1516 was designed to make direct contact with the quantum conversion layer 156 and due to production tolerances the spacer 1512 would be shorter than the combined height of the filler sheet 1516, the quantum conversion layer 156 and the camera chip 158. Equally, in this situation, the connections between the spacer 1512 and the substrate 1510 on the one side, and the spacer 1512 and the transmissive plate 154 on the other side are not exposed to high pulling forces due to production tolerances.

To avoid contamination of the lithographic apparatus by gassing out and vaporizing of the liquid, the spacer 1512 is a cylinder. The cylinder is connected to the transmissive plate 154 and the substrate 1510 with a non flexible, leak tight seal. Preventing gassing out or vaporizing of the liquid with a leak tight seal is advantageous to prevent that the sensor is left without a liquid. Without the liquid, the sensor would not be fit for use with high NA radiation anymore.

Although specific reference may be made in this text to the use of lithographic apparatus in the manufacture of ICs, it should be understood that the lithographic apparatus described herein may have other applications, such as the manufacture of integrated optical systems, guidance and detection patterns for magnetic domain memories, flat-panel displays, liquid-crystal displays (LCDs), thin-film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

Although specific reference may have been made above to the use of embodiments of the invention in the context of optical lithography, it will be appreciated that the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used herein encompass all types of electromagnetic radiation, including ultraviolet (UV) radiation (e.g. having a wavelength of or about 365, 355, 248, 193, 157 or 126 nm) and extreme ultra-violet (EUV) radiation (e.g. having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

It would be appreciated by the skilled person, that a sensor using the invention can be designed for use in a lithographic apparatus. During design of such a sensor, for instance the material of the transmissive plate (4) may be checked on gassing out, and may fulfill strict thermal expansion requirements. Also, the patterned layer (2) of chromium may be checked on compatibility with an immersion liquid to be used between the projection system and the substrate table. The design of such a sensor typically meets standards for MTBI (mean time between interrupts) and MTBF (mean time between failure) and typically can be repaired or replaced within a specified amount of time. All such considerations are normal for a sensor useable in a lithographic apparatus.

It would be appreciated by those of ordinary skill in the art that the present invention could be embodied in other specific forms without departing from the spirit or essential character thereof. The presently disclosed embodiments are therefore considered in all respects to be illustrative and not restrictive. For instance, the liquid could be an index matching liquid as well as any other appropriate liquid which is contained in the sensor. For instance the liquid could be water or Fomblin. The scope of the invention is indicated by the appended claims rather than the foregoing description, and all changes which come within the meaning and range of equivalence thereof are intended to be embraced therein. For instance, combination of the examples described above may be employed to obtain increased benefits from the invention.

We claim:

1. A sensor for a lithographic apparatus, comprising:
   a transmissive member disposable to receive radiation from a projection system of the lithographic apparatus and having a first surface;
   a luminescent member with a second surface;
   a liquid between the first surface and the second surface, wherein the first surface and the second surface are arranged to exert capillary forces on the liquid; and
   a plurality of intermediate bodies arranged between the first surface and the second surface to surround the liquid, the bodies having at least one space therebetween such that the bodies exert capillary forces on the liquid between neighboring intermediate bodies.

2. The sensor according to claim 1, wherein the sensor comprises a predetermined first area of the first surface and is arranged to exert the capillary forces via the predetermined first area of the first surface.

3. The sensor according to claim 2, wherein the first surface has a protrusion in the first area that protrudes towards the second surface.

4. The sensor according to claim 3, wherein the protrusion has a protrusion area facing the second surface.

5. The sensor according to claim 4, wherein the protrusion area is identical to the first area at the first surface.

6. The sensor according to claim 4, wherein a distance between the first surface and the second surface is constant throughout the protrusion area.

7. The sensor according to claim 4, wherein the protrusion area is substantially flat.

8. The sensor according to claim 3, wherein the protrusion has a boundary.

9. The sensor according to claim 8, wherein the protrusion area comprises a first position away from the boundary in which position the distance between the protrusion area and the second surface is smaller than the distance between the protrusion and the second surface at the boundary of the protrusion.

10. The sensor according to claim 8, wherein the protrusion area comprises a second position that is located away from the boundary where the distance between the protrusion area and the second surface is larger than the distance between the protrusion and the second surface at the boundary of the protrusion.

11. The sensor according to claim 10, wherein the sensor is arranged to transmit optical radiation to be measured via an optical volume at a predetermined position between the first surface and the second surface which optical volume is completely filled with the liquid, and in that the first surface and the second surface are arranged to pull the liquid from an overflow volume which is connected to the optical volume by a first connection area through which the liquid can flow to the optical volume by the capillary forces.

12. The sensor according to claim 11, wherein the first area of the first surface comprises an optical area that is optimized to transmit optical radiation to be measured by the sensor and the first area comprising a barrier area surrounding the optical area, wherein higher capillary forces are exerted via the barrier area than through the optical area.

13. The sensor according to claim 12, wherein a first treatment area in the first area of the first surface has received a first treatment increasing the capillary forces exerted by the first surface on the liquid.

14. The sensor according to claim 13, wherein the first treatment area is coated with a hydrophilic coating.

15. The sensor according to claim 14, wherein a second treatment area in the first surface that is outside the first area has received a second treatment decreasing the capillary forces exerted by the first surface on the liquid.

16. The sensor according to claim 15, wherein the second treatment area is coated with a hydrophobic coating.

17. The sensor according to claim 16, wherein the sensor comprises an intermediate part between the first surface and the second surface, the intermediate part comprising a third surface facing the first surface, and being arranged to exert capillary forces on the liquid between the first surface and the third surface.

18. The sensor according to claim 1, wherein at least one of the intermediate bodies has a substantially spherical shape.

19. The sensor according to claim 1, wherein the sensor comprises one or more additional intermediate bodies that are located inside an overflow volume.

20. The sensor according to claim 19, wherein the liquid has an index of refraction that matches the index of refraction of one of the first surface and the second surface.

21. The sensor according to claim 20, wherein the sensor is arranged to measure radiation intensities.

22. The sensor according to claim 21, wherein the sensor comprises a structure arranged to receive optical radiation having an optical axis and wherein the structure is arranged to periodically substantially transmit and substantially block the optical radiation, wherein the period is perpendicular to the optical axis.

23. A sensor for a lithographic apparatus, comprising:
a first surface;
a second surface, wherein the sensor includes a transmissive member disposable to receive radiation from a projection system of the lithographic apparatus and a luminescent member having a liquid fixed between the transmissive member and the second surface of the luminescent member due to capillary forces; and
a plurality of intermediate bodies arranged between the first surface and the second surface to surround the liquid, the bodies having at least one space therebetween such that the bodies exert capillary forces on the liquid between neighboring intermediate bodies.

24. The sensor according to claim 23, wherein the transmissive member has a first surface and that the luminescent member has a second surface, and wherein the transmissive member has a protrusion of the first surface protruding towards the second surface, the protrusion being arranged to increase fixation of the liquid by capillary forces on the liquid.

25. The sensor according to claim 23, wherein the first surface is at least partially treated to increase the capillary forces between the first surface and the second surface.

26. The sensor according to claim 23, wherein the first surface is at least partially treated to decrease the capillary forces between the first surface and the second surface.

27. The sensor according to claim 23, wherein the sensor comprises an intermediate part having a third surface located between the first surface and the second surface, the third surface facing the first surface, and being arranged to exert capillary forces on the liquid between the first surface and the third surface.

28. The sensor according to claim 23, wherein the transmissive member is a transmissive plate.

29. The sensor according to claim 23, wherein the luminescent member comprises at least one volume of luminescent material.

30. The sensor according to claim 23, wherein the sensor is a transmission image sensor.

31. The sensor according to claim 23, wherein the sensor is a wavefront sensor.

32. The sensor according to claim 23, wherein the sensor is arranged to measure DUV radiation.

33. A lithographic apparatus, comprising a sensor according to claim 1.

* * * * *